(12) United States Patent
Wiemker et al.

(10) Patent No.: US 10,515,478 B2
(45) Date of Patent: *Dec. 24, 2019

(54) IMAGE DATA PROCESSING

(71) Applicant: KONINKLIJKE PHILIPS N.V., Eindhoven (NL)

(72) Inventors: Rafael Wiemker, Kisdorf (DE); Tobias Klinder, Uelzen (DE); Martin Bergtholdt, Hamburg (DE); Cristian Lorenz, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/822,482

(22) Filed: Nov. 27, 2017

(65) Prior Publication Data
US 2018/0075642 A1    Mar. 15, 2018

Related U.S. Application Data

(63) Continuation of application No. 15/100,994, filed as application No. PCT/IB2014/066413 on Nov. 28, 2014, now Pat. No. 9,858,705.
(Continued)

(51) Int. Cl.
*G06T 15/08*    (2011.01)
*A61B 6/03*    (2006.01)
(Continued)

(52) U.S. Cl.
CPC .............. *G06T 15/08* (2013.01); *A61B 6/032* (2013.01); *A61B 6/5235* (2013.01);
(Continued)

(58) Field of Classification Search
None
See application file for complete search history.

(56) References Cited

U.S. PATENT DOCUMENTS 8,938,110 B2   1/2015  Goshen
2007/0262989 A1  11/2007  Buyanovskiy
(Continued)

FOREIGN PATENT DOCUMENTS

CN    1818974    8/2006
JP    2008136630    6/2008
(Continued)

OTHER PUBLICATIONS

Neumann, et al., "Gradient Estimation in Volume Data using 4D Linear Regression", EuroGraphics 2000.
(Continued)

*Primary Examiner* — Yanna Wu
(74) *Attorney, Agent, or Firm* — Larry Liberchuk

(57) ABSTRACT

A method for processing image data includes obtaining a first set of 3D volumetric image data. The 3D volumetric image data includes a volume of voxels. Each voxel has an intensity. The method further includes obtaining a local voxel noise estimate for each of the voxels of the volume. The method further includes processing the volume of voxels based at least on the intensity of the voxels and the local voxel noise estimates of the voxels. An image data processor (124) includes a computer processor that at least one of: generate a 2D direct volume rendering from first 3D volumetric image data based on voxel intensity and individual local voxel noise estimates of the first 3D volumetric image data, or registers second 3D volumetric image data and first 3D volumetric image data based at least one individual local voxel noise estimates of second and first 3D volumetric image data sets.

14 Claims, 4 Drawing Sheets

Related U.S. Application Data

(60) Provisional application No. 61/911,503, filed on Dec. 4, 2013.

(51) Int. Cl.
| | | |
|---|---|---|
| *G06T 7/00* | (2017.01) | |
| *A61B 6/00* | (2006.01) | |
| *G06T 15/06* | (2011.01) | |
| *G06T 7/30* | (2017.01) | |

(52) U.S. Cl.
CPC ............ *G06T 7/0002* (2013.01); *G06T 7/30* (2017.01); *G06T 15/06* (2013.01); *A61B 6/466* (2013.01); *A61B 6/5223* (2013.01); *G06T 2207/10081* (2013.01); *G06T 2210/41* (2013.01)

(56) References Cited

U.S. PATENT DOCUMENTS

| | | | |
|---|---|---|---|
| 2007/0299639 A1 | 12/2007 | Weese et al. | |
| 2008/0122858 A1* | 5/2008 | Wilensky | G06T 15/503 345/592 |
| 2011/0270086 A1* | 11/2011 | Hoctor | A61B 8/4488 600/443 |
| 2012/0154400 A1* | 6/2012 | Steen | G06T 15/08 345/424 |
| 2013/0202177 A1* | 8/2013 | Bar-Aviv | G06T 11/008 382/131 |
| 2014/0270454 A1 | 9/2014 | Chen | |

FOREIGN PATENT DOCUMENTS

| | | |
|---|---|---|
| WO | 2006/082590 | 8/2006 |
| WO | 2009/156943 | 12/2009 |
| WO | 2012/001648 | 1/2012 |
| WO | 2013011418 | 1/2013 |

OTHER PUBLICATIONS

Khlebnikov, et al., "Noise-based Volume rendering for the visualization of multivariate volumetric data", 2013.

Rohde, et al., "Estimating intensity variance due to noise in registered images: Applications to diffusion tensor MRI", NeuroImage 26 (2005) 673-684.

Pan, et al., Medical Image Registration Based on SVD and Modified PSNR*; Journal of Information Science and Engineering 27, 1761-1775 (2011).

Simpson, et al., "A Probabilistic Non-Rigid Registration Framework Using Local Noise Estimates"; 2012 9th IEEE International Symposium on Biomedical Imaging (ISBI), May 2012.

Piramuthu, et al., "Penalized Maximum Likelihood Image Reconstruction with Min-Max Incorporation of Noisy Side Information", IEEE 1998.

\* cited by examiner

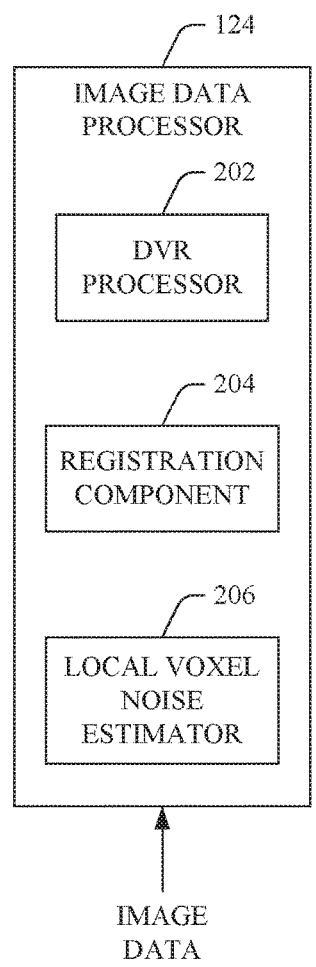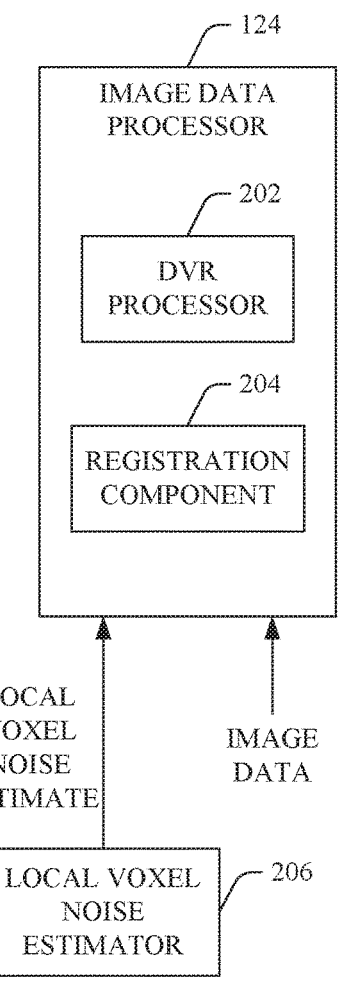
FIGURE 2
FIGURE 3

IMAGE DATA PROCESSING

CROSS REFERENCE TO RELATED APPLICATIONS

This application is a continuation application of application Ser. No. 15/100,994, filed Jun. 2, 2016, which is a national filing of PCT application Serial No. PCT/IB2014/066413, filed Nov. 28, 2014, which is incorporated herein by reference, and which claims the benefit of U.S. provisional application Ser. No. 61/911,503 filed Dec. 4, 2013, which is incorporated herein by reference.

FIELD OF THE INVENTION

The following generally relates to processing image data and more particularly to processing image data using individual local voxel noise estimates, and is described with particular application to computed tomography (CT); however, the following is also amenable to other imaging modalities such as positron emission tomography (PET), single photon emission computed tomography (SPECT), magnetic resonance (MR), ultrasound (US), and/or other imaging modality.

BACKGROUND OF THE INVENTION

A CT scanner generally includes an x-ray tube mounted on a rotatable gantry opposite a detector array located across an examination region. The rotatable gantry, and hence the x-ray tube, rotates around the examination region, and the x-ray tube emits radiation that traverses the examination region and a portion of a subject therein. The detector array detects the radiation and generates projection data indicative thereof. A reconstructor reconstructs the projection data and generates 3D volumetric image data representative of the scanned portion of the subject.

Suitable reconstruction algorithms include iterative reconstruction algorithms such as a maximum likelihood iterative reconstruction (MLIR) algorithm, etc., and non-iterative reconstruction algorithms such as filtered back projection (FBP), etc. The 3D volumetric image data includes voxels that are represented in terms of gray scale intensity values corresponding to relative radiodensity for CT (and other material qualities for MR, PET, SPECT, US, respectively). The gray scale values (intensities) reflect the attenuation characteristics of the scanned subject and/or object, and generally show structure such as anatomical structures within the scanned patient or object.

The 3D volumetric image data can be processed to create a 2D projection of the 3D volumetric image data. One such approach is direct volume rendering (DVR). With DVR, each voxel value of the 3D volumetric image data is mapped to a color value, an opacity value, and a gradient value. Once mapped, these properties are then projected from 3D volume space into 2D image space, such as the pixels of a display monitor, by combining them along view rays into rendering pixels. In another application, the 3D volumetric image data from two different image data sets can be processed to register (or spatially align) the data sets. Both applications, volume rendering and registration, are dependent on a noise estimate for the image volume(s). Unfortunately, global noise parameters may not accurately reflect the local voxel noise level, which may degrade the resulting image quality for volume rendering, and the resulting spatial accuracy for registration.

SUMMARY OF THE INVENTION

Aspects described herein address the above-referenced problems and others.

The following describes an image data processing approach that takes into account both voxel gray scale intensity values and individual local voxel noise estimates of a 3D volumetric image data set(s). Such processing includes at least one of DVR and image data registration. By taking into account the individual local voxel noise estimates, the approach described herein may improve DVR and/or registration quality, relative to a configuration in which a global noise estimate is instead utilized.

In one aspect, a method for processing image data includes obtaining a first set of 3D volumetric image data. The 3D volumetric image data includes a volume of voxels. Each voxel has an intensity. The method further includes obtaining a local voxel noise estimate for each of the voxels of the volume. The method further includes processing the volume of voxels based at least on the intensity of the voxels and the local voxel noise estimates of the voxels.

In another aspect, an image system comprises a computer processor and memory that stores image data processing instructions. The computer processor executes the image data processing instructions, which causes the computer processor to at least one of: generate a 2D direct volume rendering from first 3D volumetric image data based on voxel intensity and individual local voxel noise estimates of the first 3D volumetric image data, or register second 3D volumetric image data and first 3D volumetric image data based at least one individual local voxel noise estimates of second and first 3D volumetric image data sets.

In another aspect, a computer readable storage medium is encoded with computer readable instructions, which, when executed by a processor, causes the processor to: generate a 2D direct volume rendering from first 3D volumetric image data based on voxel intensity and individual local voxel noise estimates of the first 3D volumetric image data, or register second 3D volumetric image data and first 3D volumetric image data based at least one individual local voxel noise estimates of second and first 3D volumetric image data sets.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIG. 2 schematically illustrates an example of the image data processor, which includes a DVR processor, a registration component, and a local voxel noise estimator.

FIG. 3 schematically illustrates an example of the image data processor, which includes the DVR processor and the registration component, but does not include the local voxel noise estimator.

DETAILED DESCRIPTION OF EMBODIMENTS

Figure 1:
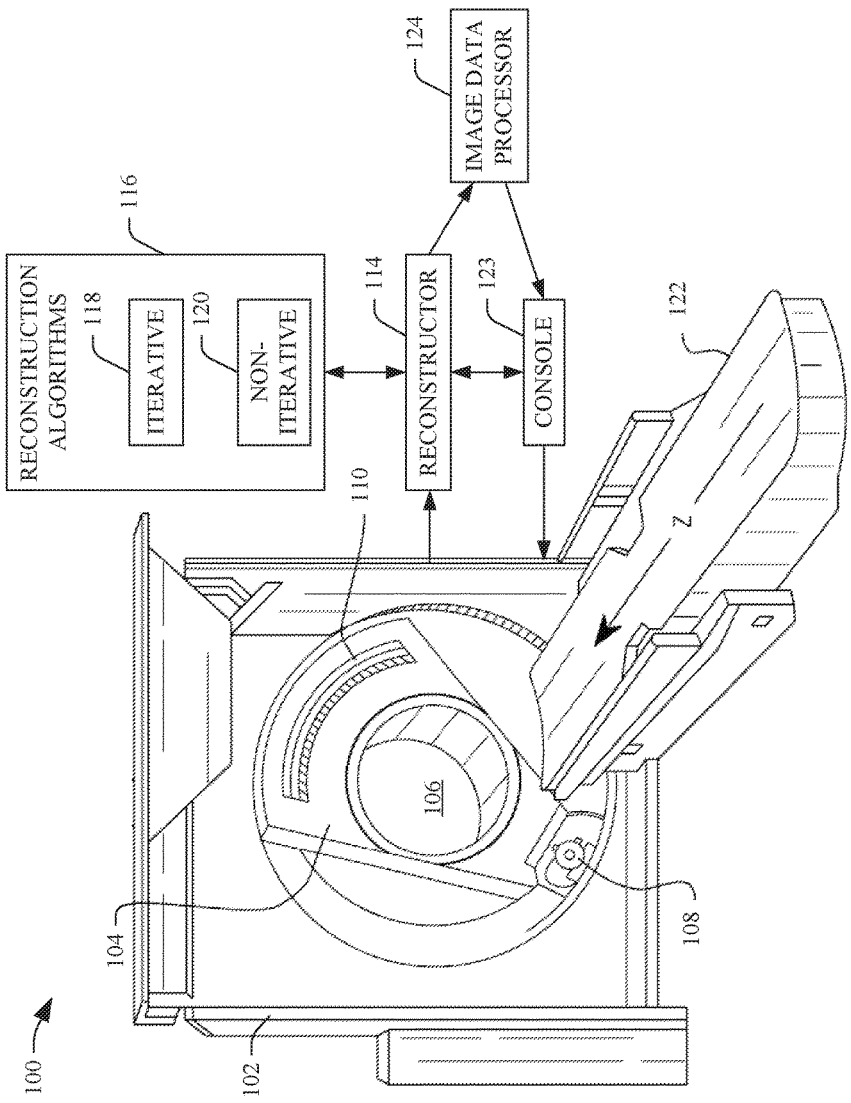
FIG. 1 schematically illustrates an example imaging system in connection with an image data processor.

FIG. 1 illustrates an imaging system 100 such as a computed tomography (CT) scanner. In another embodiments, the imaging system 100 includes as positron emission tomography (PET), single photon emission computed tomography (SPECT) and/or other scanner. The illustrated imaging system 100 includes a stationary gantry 102 and a rotating gantry 104, which is rotatably supported by the stationary gantry 102. The rotating gantry 104 rotates around an examination region 106 about a longitudinal or z-axis.

A radiation source 108, such as an x-ray tube, is supported by the rotating gantry 104 and rotates with the rotating gantry 104 about the examination region 106, and emits radiation that traverses the examination region 106. A one or two dimensional radiation sensitive detector array 110, located opposite the radiation source 108 across the examination region 106, includes one or more rows of detector pixels arranged along the z-axis. The detector pixels detect radiation traversing the examination region 106 and generate a signal or projection data indicative thereof.

A reconstructor 114 reconstructs the projection data and generates 3D volumetric image data indicative of the examination region 106. In the illustrated example, the reconstructor 114 can employ one or more reconstruction algorithms 116, including, but not limited to an iterative reconstruction algorithm(s) 118 and a non-iterative reconstruction algorithm(s) 120. The iterative reconstruction algorithm(s) 118 includes algebraic, statistical, and/or other iterative reconstruction algorithm(s). Furthermore, the iterative reconstruction algorithm(s) 118 may determine and/or utilize a projection domain and/or an image domain individual local voxel noise estimate for a reconstruction.

By way of example, an iterative image reconstruction algorithm has been based on a cost function with a data comparison term and an image noise penalty term. A general formulation of such a cost function is: $\psi(x)=-L(Ax|y)+\beta \cdot R(x)$, where $\psi(x)$ represents the cost function, $L(Ax|y)$ represents a likelihood term that compares a forward projected image (Ax, where A is a forward projection operator and x is the image) to measured data (y), R(x) represents a roughness penalty term that penalizes noise (or "roughness") in the reconstructed image (x), and $\beta$ represents a regularization term that controls a strength of the regularization.

With the above iterative image reconstruction approach, individual local voxel noise estimates are determined. An example of such an algorithm is described in Goshen et al., serial number U.S. Ser. No. 13/508,751, filed on Oct. 29, 2010, and entitled "Enhanced image data/dose reduction," the entirety of which is incorporated herein by reference. Other iterative image reconstruction algorithms are also contemplated herein.

A support 122, such as a couch, supports a subject in the examination region 106 and can be used to position the subject with respect to x, y, and/or z axes before, during and/or after scanning. A computing system serves as an operator console 123, and includes an output device such as a display and an input device such as a keyboard, mouse, and/or the like. Software resident on the operator console 123 allows the operator to control the operation of the system 100. Such control includes selecting an acquisition protocol, initiation scanning, identifying a reconstruction algorithm, etc.

An image data processor 124 is configured to process the image data. In one instance, this at least includes reformatting the image data to project the 3D volumetric image data (voxels) into 2D space such as the pixels of a display monitor and/or registering image data sets (e.g., 3D and/or 2D). As described in greater detail below, in one instance, the image data processor 124 employs individual local voxel noise estimates with such processing. The individual local voxel noise estimates can be determined by the reconstructor (e.g., during an iterative reconstruction using noise estimates), the image data processor 124, and/or other device.

It is to be appreciated that the image data processor 124 can be implemented via one or more computer processors (e.g., a central processing unit (CPU), a microprocessor, etc.) executing one or more computer executable instructions embedded or encoded on computer readable storage medium (which excludes transitory medium) such as physical memory. However, at least one of the computer executable instructions can alternatively be carried by a carrier wave, signal, and other transitory medium and implemented via the one or more computer processors.

FIG. 2 schematically illustrates a non-limiting example of the image data processor 124. With this example, the image data processor 124 receives image data, but no individual local voxel noise estimates, and estimates the individual local voxel noise estimates. The illustrated image data processor 124 includes a DVR processor 202, a registration component 204, and a local voxel noise estimator 206.

FIG. 3 illustrates a variation of FIG. 2 in which the image data processor 124 also receives the individual local voxel noise estimates. With the example, the local voxel noise estimator 206 is omitted from the image data processor 124 and is located in a device remote and distinct from the image data processor. The local voxel noise estimator 206 can be part of the reconstructor 114 (FIG. 1) and/or other apparatus.

With reference to FIGS. 2 and 3, the DVR processor 202, for each pixel in the 2D projection image, casts a view ray through the 3D volumetric image data. At each step along the view ray, a local color (e.g., a vector), a local opacity (e.g., a scalar), and a local gradient (e.g., a vector) is computed. These three magnitudes are then combined along the view ray into a rendered pixel of the 2D rendering image. A non-limiting example of a suitable combination approach is discussed in Charles D. Hansen et al., "The Visualization Handbook" (2005). Other approaches are contemplated therein.

Figures 4, 5:
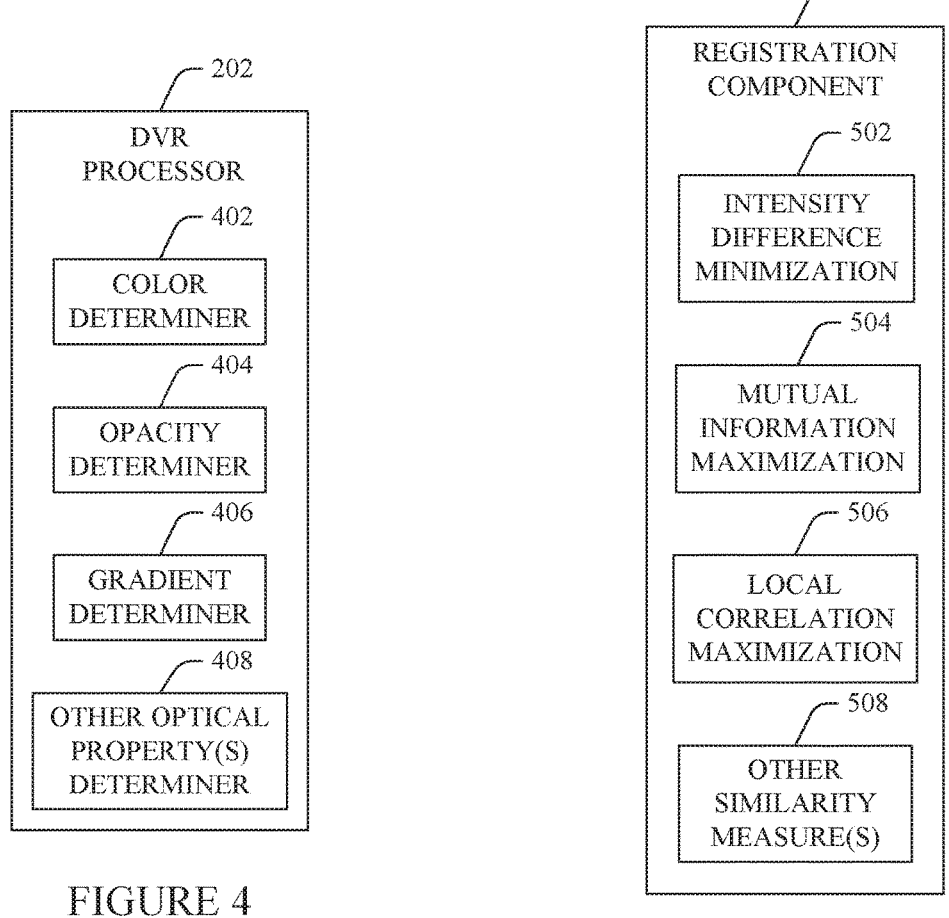
FIG. 4 schematically illustrates an example of the DVR processor.
FIG. 5 schematically illustrates an example of the registration component.

Briefly turning to FIG. 4, a non-limiting example of the DVR processor 202 is illustrated. The DVR processor 202 includes at least a color determiner 402, an opacity determiner 404, and a gradient determiner 406. Optionally, the DVR processor 202 includes another optical property(s) determiner 408. In comparison with conventional approaches, the DVR processor 202 computes the local voxel color in the same way as in standard DVR, but a local voxel opacity and a local voxel gradient, in contrast, take into account the individual local voxel noise estimate for each voxel. This is described in greater detail next.

The opacity determiner 404 determines an opacity value for a voxel based on the intensity for that voxel and the individual local voxel noise estimate for that voxel. A non-limiting example is discussed next. A local opacity $O(x)$ for a voxel is first computed as in standard-DVR (e.g., from an opacity transfer function). Then, the local opacity $O(x)$ value is multiplied with a confidence value $C(x)$ in the interval [0 ... 1]. C(x) is derived from the individual local voxel noise estimate σ(x) using a monotonous decreasing function. An example of such a function is the following Gaussian function: $C=\exp(-0.5*\sigma^2/\sigma_o^2)$, where $\sigma^2$ is the local voxel noise estimate and $\sigma_o^2$ is the global noise estimate.

The gradient determiner 406 determines a gradient value for a voxel based on the intensity of neighboring voxels and the individual local voxel noise estimate for the neighboring voxels. A non-limiting example is discussed next. The local gradient (conventionally computed from central differences in x, y, z) is computed as a weighted linear fit, with the weights given by the local confidence values C(x). The noise-weighted fit can optionally be a weighted line fit in x, y, z, direction separately (axis-parallel 1D-neighborhood), a weighted plane fit in the 3D neighborhood, and/or otherwise. The so-determined gradient vector is then used to control the shading of the rendering. The color determiner 402 determines the local color for a voxel without considering the local voxel noise estimate.

The basic underlying concept is that voxels with a high noise level become comparatively transparent in the rendering (i.e. are assigned a lower opacity value) and voxels with low noise level become comparatively opaque (i.e. are assigned a higher opacity value). Additionally, the local gradients are estimated taking into account the relative reliability of neighboring voxels, resulting in improved shading in the resulting rendering. Furthermore, the colors of the rendering are not changed by the local noise estimate.

This rendering technique processes two input volumes (the image data and the individual local voxel noise estimates), and cannot be achieved by simply multiplying the intensity volume with the confidence volume and providing the result as an input into the standard rendering engine.

Returning to FIGS. 2 and 3, the registration component 204 registers at least two sets of image data (in 3D and/or 2D space). Briefly turning to FIG. 5, the illustrated registration component 204 includes at least one of an intensity difference minimization algorithm 502, a mutual information maximization algorithm 504, a local correlation maximization algorithm 506, and/or other similarity measure algorithm(s) 508.

With the intensity difference minimization algorithm 502, the registration component 204 registers images based on minimization of intensity deviations, for example, using a sum of squared differences. However, instead of minimizing the simple sum of differences in intensities $I_1$ and $I_2$ for all spatial positions x: $\Sigma(I_1-I_2)^2$, the registration component 204 minimizes the sum of error weighted differences $\Sigma[I_1-I_2)^2/(\sigma_1^2+\sigma_2^2)]$, where $\sigma^1$ and $\sigma^2$ are the local voxel noise estimates of the two voxels from the two image data sets.

With the mutual information maximization algorithm 504, the registration component 204 registers images based on a maximization of mutual information: The mutual information can be computed as a negative entropy $\Sigma$ H log H of the bivariate histogram H(I1, I2). For the standard algorithm, this histogram H is incremented by +1 for every incidence of the intensities I1 and I2 at the corresponding locations in the two images. In contrast, the registration component 204 increments the bivariate histogram by a locally dependent confidence value c(x). In one non-limiting instance, $c(x)=\exp(-0.5*(\sigma_1^2+\sigma_2^2)/\sigma_o^2)$, which weights in an inverse way to the local error estimates $\sigma_1(x)$ and $\sigma_2(x)$ of the voxels of the two image data sets, and where $\sigma_o^2$ is the global noise estimate.

With the local correlation maximization algorithm 506, the registration component 204 registers images based on a maximization of a local correlation. A non-weighted linear correlation (LC) can be computed as shown in EQUATION 1:

$$LC_i(I_1, I_2) = \frac{cov_i(I_1, I_2)^2}{cov_i(I_1, I_1)*cov_i(I_2, I_2)}, \quad \text{EQUATION 1}$$

where $cov_i(I_1, I_2)=\Sigma_{l \in S_i} I'_{1,l} I'_{2,l}$ and $l \in S_i$ is a local neighborhood. The registration component 204 computes the covariance and variances using spatially varying weights w(x) such that $cov_i(I_1, I_2)=\Sigma_{l \in S_i} w_{1,l} I'_{1,l} w_{2,l} I'_{2,l}/\Sigma_{l \in S_i} w_{1,l} w_{2,l}$. The weights are computed through $\exp(-0.5*r^2/\sigma_r^2)$, depending only on a radial Euclidean distance $r=|x-x_i|$ from the center point $x_o$, and then multiplying the spatial weights w(x) with a confidence value c(x). In one non-limiting instance, $c(x)=\exp(-0.5*(\sigma_1^2+\sigma_2^2)/\sigma_o^2)$, which is inverse to the local error estimates $\sigma_1(x)$ and $\sigma_2(x)$.

The algorithms 502, 504, 506, and 508 operate in a manner as to vary the spatial displacement field until a certain similarity measure is maximized or minimized. The basic underlying concept is that voxels with a higher local noise level have comparatively less influence on the similarity measure and thus on the outcome of the registration, and the voxels with lower local noise level get comparatively more influence. Generally, the algorithms 502, 504, 506, and 508 meaningfully accommodate the voxelwise noise level estimation σ(x) in addition to the standard image intensities I(x).

With continuing reference to FIG. 2, the local voxel noise estimator 206 can employ known and/or other voxel noise estimation approaches. An example of a suitable noise estimation from image data is described in Goshen et al., serial number U.S. Ser. No. 13/508,751, filed on Oct. 29, 2010, and entitled "Enhanced image data/dose reduction." Other voxel noise estimations are also contemplated herein. This also includes projection domain approaches.

Figure 6:
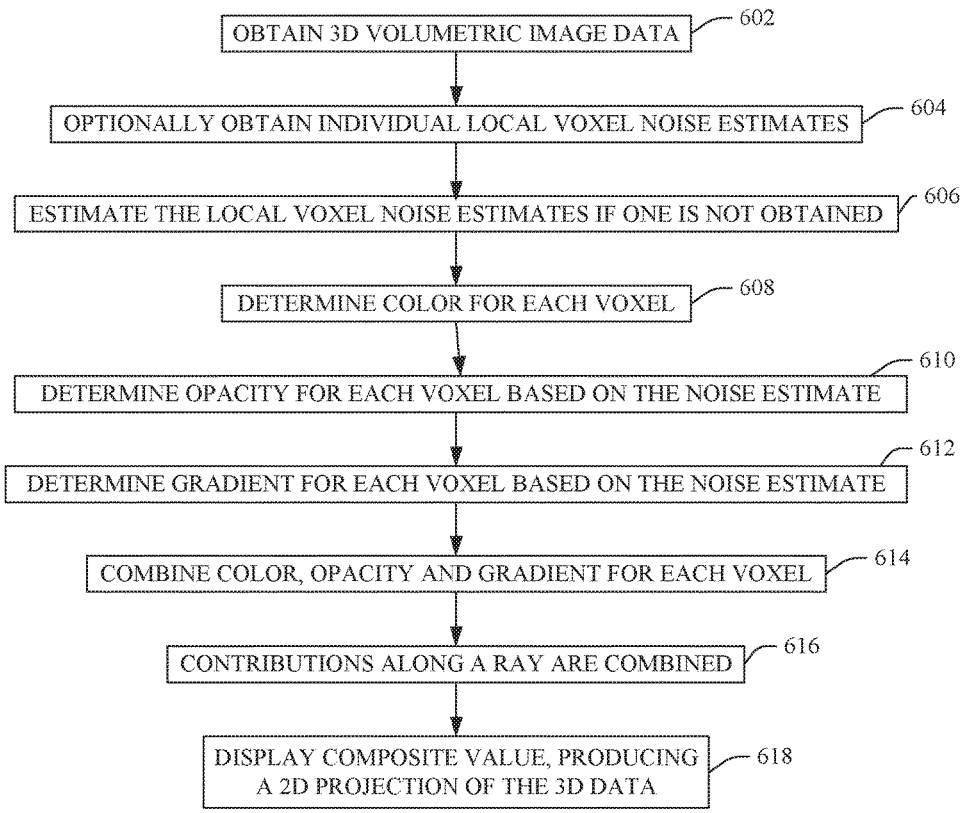
FIG. 6 illustrates an example method for generating a DVR image based on 3D volumetric image data and individual local voxel noise estimates for the individual voxels of the 3D volumetric image data.

FIG. 6 illustrates an example method for generating a DVR image based on 3D volumetric image data and noise estimates for the individual voxels.

It is to be appreciated that the ordering of the acts of these methods is not limiting. As such, other orderings are contemplated herein. In addition, one or more acts may be omitted and/or one or more additional acts may be included.

At 602, 3D volumetric image data is obtained.

At 604, optionally, an individual local voxel noise estimate, for each of at least a sub-set of the voxels of the 3D volumetric image data, is obtained.

At 606, if act 604 is omitted, the individual local voxel noise estimates are estimated, as discussed herein and/or otherwise.

At 608, a color value for each voxel of the image data is determined. As discussed herein, in one instance, a local color is determined for each voxel without considering the local voxel noise estimate.

At 610, an opacity for each voxel is determined based on the intensity for the voxel and the individual local voxel noise estimate for the voxel, as described herein or otherwise.

At 612, a gradient value for each voxel based on the intensity of neighboring voxels and the individual local voxel noise estimate for the voxel.

At 614, the color value, the opacity value, and the gradient value for each voxel are combined to generate a contribution of the voxel to a projection view ray through the 3D volume.

At 616, voxel-wise contributions along a view ray are combined to generate a rendering pixel for the view ray.

At 618, the composite values are rendered, producing a 2D projection of the 3D volumetric image data.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

Figure 7:
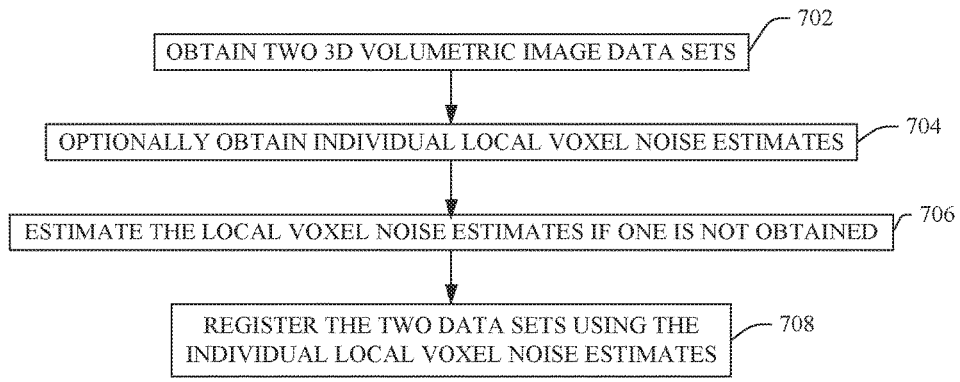
FIG. 7 illustrates an example method for registering two different image data sets based on two 3D volumetric image data sets and individual local voxel noise estimates for the individual voxels of each of the two 3D volumetric image data sets.

FIG. 7 illustrates an example method for registering two different image data sets based on two 3D volumetric image data sets and noise estimates for the individual voxels of each of the two 3D volumetric image data sets.

It is to be appreciated that the ordering of the acts of these methods is not limiting. As such, other orderings are contemplated herein. In addition, one or more acts may be omitted and/or one or more additional acts may be included.

At 702, two 3D volumetric image data sets are obtained. As discussed herein, the two data sets can be from the same modality, but acquired at different points in time, or different modalities.

At 704, optionally, an individual local voxel noise estimate, for each of at least a sub-set of the voxels of both of the 3D volumetric image data, is obtained.

At 706, if act 704 is omitted, the individual local voxel noise estimates are estimated, as discussed herein and/or otherwise.

At 708, the two 3D volumetric image data sets obtained are spatially registered based on the individual local voxel noise estimates, as described herein and/or otherwise.

The above may be implemented by way of computer readable instructions, encoded or embedded on computer readable storage medium (which excludes transitory medium), which, when executed by a computer processor(s) (e.g., central processing unit (cpu), microprocessor, etc.), cause the processor(s) to carry out acts described herein. Additionally, or alternatively, at least one of the computer readable instructions is carried by a signal, carrier wave or other transitory medium, which is not computer readable storage medium.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method, comprising:
   receiving, with a processor, 3D volumetric image data, which includes a plurality of voxels, each voxel of the 3D volumetric image data having an intensity, wherein the 3D volumetric image data is produced by one of a computed tomography, a positron emission tomography and a single photon emission computed tomography;
   determining, with the processor, a local voxel noise estimate for each voxel of the 3D volumetric image data;
   determining, with the processor and for each voxel of the 3D volumetric image data, a weighted gradient value as a weighted linear fit or a weighted planar fit with weights given by local confidence values, which are determined as a function of a ratio of the local voxel noise estimate of each voxel of the 3D volumetric image data and a global noise estimate; and
   processing, with the processor, the plurality of voxels by combining, for each voxel of the 3D volumetric image data, a color value, an opacity value and the weighted gradient value to generate a noise-weighted rendering contribution for each voxel of the 3D volumetric image data.

2. The method of claim 1, further comprising:
   for each voxel of the 3D volumetric image data, determining a local confidence value as $\exp(-0.5*\sigma^2/\sigma_o^2)$, where $\sigma^2$ is the local voxel noise estimate and $\sigma_o^2$ is the global noise estimate.

3. A method, comprising:
   receiving, with a processor, 3D volumetric image data, which includes a plurality of voxels, each voxel of the 3D volumetric image data having an intensity, wherein the 3D volumetric image data is produced by one of a computed tomography, a positron emission tomography and a single photon emission computed tomography;
   determining, with the processor, a local voxel noise estimate for each voxel of the 3D volumetric image data;
   determining, with the processor and for each voxel of the 3D volumetric image data, an initial opacity value from an opacity transfer function;
   determining, with the processor and for each voxel of the 3D volumetric image data, a confidence value based on a ratio of the local voxel noise estimate and a global noise estimate;
   determining, with the processor and for each voxel of the 3D volumetric image data, a weighted opacity value by multiplying the initial opacity value by the confidence value in an interval of zero to one; and
   processing, with the processor, the plurality of voxels by combining, for each voxel of the 3D volumetric image data, a color value, the weighted opacity value and a gradient value to generate a noise-weighted rendering contribution for each voxel of the 3D volumetric image data.

4. The method of claim 3, further comprising:
   for each voxel of the 3D volumetric image data, determining the confidence value as $\exp(-0.5*\sigma^2/\sigma_o^2)$, where $\sigma^2$ is the local voxel noise estimate and $\sigma_o^2$ is the global noise estimate.

5. An image data processor, comprising:
   a processor; and
   a memory configured to store image data processing instructions, wherein the processor is configured to execute the image data processing instructions, which cause the processor to:

obtain first 3D volumetric image data, which includes a plurality of voxels, each voxel of the first 3D volumetric image data having an intensity, wherein the first 3D volumetric image data is produced by one of a computed tomography, a positron emission tomography and a single photon emission computed tomography;

determine a local voxel noise estimate for each voxel of the first 3D volumetric image data;

determine, for each voxel of the first 3D volumetric image data, a weighted gradient value as a weighted linear fit or a weighted planar fit with weights given by local confidence values, which are determined as a function of a ratio of the local voxel noise estimate of each voxel of the first 3D volumetric image data and a global noise estimate; and process the plurality of voxels by combining, for each voxel of the first 3D volumetric image data, a color value, an opacity value and the weighted gradient value to generate a noise-weighted rendering contribution for each voxel of the first 3D volumetric image data.

6. The image data processor of claim 5, wherein the processor is configured to determine, for each voxel of the first 3D volumetric image data, the weighted gradient value as the weighted linear fit in x, y, z.

7. The image data processor of claim 5, wherein the processor is configured to determine, for each voxel of the first 3D volumetric image data, the weighted gradient value as the weighted planar fit in a three-dimensional neighborhood.

8. The image data processor of claim 5, wherein the processor is configured to compute, for each voxel of the first 3D volumetric image data, a local confidence value as $\exp(-0.5*\sigma^2/\sigma_o^2)$, where $\sigma^2$ is the local voxel noise estimate and $\sigma_o^2$ is the global noise estimate.

9. The image data processor of claim 8, wherein the local confidence value of each voxel of the first 3D volumetric image data has a value in an interval of zero to one.

10. The image data processor of claim 5, wherein the processor is configured to employ a gradient vector to control a shading of the noise-weighted rendering contribution for each voxel of the first 3D volumetric image data.

11. The image data processor of claim 5, wherein the processor is configured to determine a local color for a voxel without considering a local noise estimate of the voxel.

12. The image data processor of claim 5, wherein the processor is configured to determine a local opacity for a voxel from an opacity transfer function by multiplying the local opacity with a local confidence value.

13. The image data processor of claim 5, wherein the processor is configured to obtain second 3D volumetric image data, which include a second plurality of voxels, each voxel of the second 3D volumetric image data having an intensity, obtain a local voxel noise estimate for each voxel of the second 3D volumetric image data, and register the first and second 3D volumetric image data based at least on a registration algorithm that includes a bivariate histogram incremented by a value.

14. The image data processor of claim 13, wherein the processor computes the value as $\exp(-0.5*(\sigma_1^2+\sigma_2^2)/\sigma_o^2)$, where $\sigma_1^2$ is an individual local voxel noise estimate of a voxel of the first 3D volumetric image data, $\sigma_2^2$ is an individual local voxel noise estimate of a voxel of the second 3D volumetric image data, and $\sigma_0^2$ is the global noise estimate.

* * * * *